United States Patent
Mertoglu et al.

(10) Patent No.: US 9,591,854 B2
(45) Date of Patent: Mar. 14, 2017

(54) AGROFORMULATIONS CONTAINING A LACTONE BASED ALKOXYLATE

(71) Applicant: BASF SE, Ludwigshafen (DE)

(72) Inventors: Murat Mertoglu, Ludwigshafen (DE); Rainer Berghaus, Speyer (DE); Andreas Kunst, Ludwigshafen (DE); Benedikt Crone, Mannheim (DE); Christian Koenig, Mannheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/407,653

(22) PCT Filed: Jun. 6, 2013

(86) PCT No.: PCT/EP2013/061648
§ 371 (c)(1),
(2) Date: Dec. 12, 2014

(87) PCT Pub. No.: WO2013/189745
PCT Pub. Date: Dec. 27, 2013

(65) Prior Publication Data
US 2015/0230461 A1   Aug. 20, 2015

Related U.S. Application Data

(60) Provisional application No. 61/660,857, filed on Jun. 18, 2012.

(30) Foreign Application Priority Data

Jun. 18, 2012 (EP) .................................. 12172438

(51) Int. Cl.
*A01N 37/36* (2006.01)
*A01N 43/653* (2006.01)
*A01N 43/56* (2006.01)
*C07C 69/708* (2006.01)

(52) U.S. Cl.
CPC ............. *A01N 37/36* (2013.01); *A01N 43/56* (2013.01); *A01N 43/653* (2013.01); *C07C 69/708* (2013.01)

(58) Field of Classification Search
CPC ...... A01N 37/36; A01N 43/56; A01N 43/653; C07C 69/708
USPC .......................................... 504/100; 514/383
See application file for complete search history.

(56) References Cited

U.S. PATENT DOCUMENTS

| 3,284,417 | A | 11/1966 | Hostettler et al. |
| 6,887,592 | B2 | 5/2005 | Hieda et al. |
| 6,887,952 | B1 | 5/2005 | Buechler et al. |
| 2003/0158044 | A1 | 8/2003 | Wollenweber et al. |
| 2005/0170968 | A1 | 8/2005 | Berghaus et al. |
| 2008/0176921 | A1* | 7/2008 | Sanson ................. A01N 25/04 514/407 |

FOREIGN PATENT DOCUMENTS

| CN | 1360062 | 11/2005 |
| EP | 2 384 624 | 11/2011 |
| JP | 5 255584 | 10/1993 |
| JP | 6 122655 | 5/1994 |
| JP | 7048450 | 2/1995 |
| JP | 2004 331642 | 11/2004 |
| JP | 2004331642 A | * 11/2004 |
| WO | WO 97/03106 | 1/1997 |
| WO | WO 01/04183 | 1/2001 |
| WO | WO 01/76368 | 10/2001 |
| WO | WO 02/098232 | 12/2002 |
| WO | WO 03/090531 | 11/2003 |
| WO | WO 2009/055014 | 4/2009 |
| WO | WO 2009/064459 | 5/2009 |
| WO | WO 2010/072341 | 7/2010 |
| WO | WO 2011/071492 | 6/2011 |

OTHER PUBLICATIONS

Basile, Tiziana et al. "Condensation of Redormatsku reagents with acetals in the presence of TiCl₄; a novel entry to enantiomerically-enriched β-hydroxy-esters", J. Chem. Soc., Chem Commun, 1989, p. 596-597.
Basile, Tiziana et al., "Synthesis of 3-alkoxyalkanoic esters from acetals, a novel application of reformatsky reagents in asymmetric synthesis", Synthesis, Apr. 1990, p. 305-311.
International Preliminary Report on Patentability dated Oct. 6, 2014, prepared in International Application No. PCT/EP2013/061648.
International Search Report dated Dec. 11, 2013, prepared in International Application No. T/EP2013/061648.
European Search Report dated Mar. 7, 2013, prepared in European Application No. 12172438.
Pöselt, Elmar, et al., "Highly stable biocomatble inorganic nanoparticles by self-assembly of triblock copolymer ligands", Langmuir, 2009, p. 13906-13913, vol. 25, No. 24.
Wu, Gang et al., "Well defined amphiphilic biodegradable comb like graft copolymers: their unique architecture-determined LCST and UCST thermoresponsivity", Macromolecules, 2011, p. 999-1008, vol. 44.

* cited by examiner

*Primary Examiner* — Janet Epps-Smith
*Assistant Examiner* — Courtney Brown
(74) *Attorney, Agent, or Firm* — Brinks Gilson & Lione

(57) ABSTRACT

The present invention relates to composition comprising a pesticide and an alkoxylate of the formula (I) as defined below. The invention further relates to said alkoxylate. The invention further relates to a method of preparing said composition by bringing the alkoxylate and the pesticide into contact. Finally, the invention relates to a method of controlling phytopathogenic fungi and/or undesired plant growth and/or undesired insect or mite attack and/or for regulating the growth of plants, wherein said composition is allowed to act on the respective pests, their environment or the crop plants to be protected from the respective pest, on the soil and/or on undesired plants and/or on the crop plants and/or on their environment; and to seed containing said composition.

17 Claims, No Drawings

AGROFORMULATIONS CONTAINING A LACTONE BASED ALKOXYLATE

This application is a National Stage application of International Application No. PCT/EP2013/061648, filed Jun. 6, 2013, which claims the benefit of U.S. Provisional Application No. 61/660,857, filed Jun. 18, 2012, the entire contents of which are hereby incorporated herein by reference. This application also claims priority under 35 U.S.C. §119 to European Patent Application No. 12172438.9, filed Jun. 18, 2012, the entire contents of which is hereby incorporated herein by reference.

DESCRIPTION

The present invention relates to composition comprising a pesticide and an alkoxylate of the formula (I) as defined below. The invention further relates to said alkoxylate. The invention further relates to a method of preparing said composition by bringing the alkoxylate and the pesticide into contact. Finally, the invention relates to a method of controlling phytopathogenic fungi and/or undesired plant growth and/or undesired insect or mite attack and/or for regulating the growth of plants, wherein said composition is allowed to act on the respective pests, their environment or the crop plants to be protected from the respective pest, on the soil and/or on undesired plants and/or on the crop plants and/or on their environment; and to seed containing said composition. The preferred embodiments of the invention mentioned herein below have to be understood as being preferred either independently from each other or in combination with one another.

Agroformulations containing pesticide and alkoxylated alkanols are known from US 2005/0170968.

Alkoxylates are important agroformulation auxiliaries and assist in improving the stability of the formulation and the efficacy of the pesticide. It is an ongoing challenge to identify new auxiliaries with improved properties.

Object of the present invention was to overcome the problems of the state of the art. The object was solved by a composition comprising a pesticide and an alkoxylate of the formula (I)

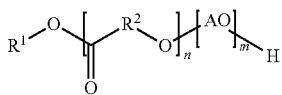

where $R^1$ is a $C_1$-$C_{32}$ hydrocarbon group, $R^2$ is a $C_2$-$C_{20}$ aliphatic hydrocarbon group, AO is $C_2$-$C_6$ alkyleneoxy group, n is from 1 to 30, and m is from 1 to 200. In another form the object was solved by a composition comprising a pesticide and an alkoxylate of the formula (I) where $R^1$ is a $C_6$-$C_{32}$ hydrocarbon group, $R^2$ is a linear saturated $C_3$-$C_{15}$ aliphatic hydrocarbon group, AO is $C_2$-$C_6$ alkyleneoxy group, n is from 1 to 30, and m is from 2 to 200.

The present invention further relates to the alkoxylate of the formula (I).

$R^1$ is usually a monovalent $C_1$-$C_{32}$ hydrocarbon group, preferably a monovalent $C_2$-$C_{20}$ hydrocarbon group. More preferably, $R^1$ is a linear or branched, saturated or unsaturated $C_1$-$C_{32}$ alkyl (preferably $C_2$-$C_{20}$ alkyl and in particular $C_{10}$-$C_{18}$ alkyl), or a mixture thereof. In another form $R^1$ is usually a monovalent $C6$-$C_{32}$ hydrocarbon group, preferably a monovalent $C_6$-$C_{20}$ hydrocarbon group. More preferably, $R^1$ is a linear or branched, saturated or unsaturated $C_6$-$C_{32}$ alkyl (preferably $C_8$-$C_{20}$ alkyl and in particular $C_{10}$-$C_{18}$ alkyl), or a mixture thereof.

$R^1$ is preferably a linear or branched, saturated alkyl residue. In another preferred form, $R^1$ is a branched saturated alkyl residue.

Typical examples for $R^1$ are linear or branched butyl, hexyl, heptyl, octyl, nonyl, decyl, undecyl, dodecyl, tridecyl, hexadecyl, heptadecyl and octadecyl, or mixture of the aforementioned residues. In another form typical examples for $R^1$ are linear or branched hexyl, heptyl, octyl, nonyl, decyl, undecyl, dodecyl, tridecyl, hexadecyl, heptadecyl and octadecyl, or mixture of the aforementioned residues.

In a preferred form, $R^1$ is a mixture of isomeric tridecanols, which are commercially available as Isotridecanol N from BASF SE, CAS Nr. 27458-92-0. In another preferred form, $R^1$ is a branched decyl, such as 2-propylheptyl. In another preferred form, $R^1$ is 1-hexadeanol.

$R^2$ is usually a divalent $C_2$-$C_{20}$ aliphatic hydrocarbon group, preferably a divalent $C_3$-$C_{15}$ aliphatic hydrocarbon group. More preferably, $R^2$ is a linear, saturated $C_2$-$C_{20}$ alkylene, wherein $C_3$-$C_{15}$ alkylene is even more preferred. In particular $R^2$ is a linear saturated $C_4$-$C_{10}$ alkylene, wherein $C_4$-$C_8$ alkylene is even more preferred.

In an especially preferred form, $R^2$ is a $C_5$ pentylene resulting in the alkoxylate of the formula (II)

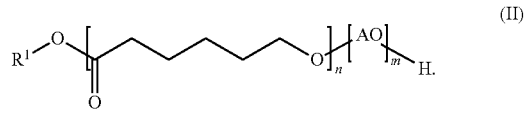

Preferably, in the alkoxylate of the formula (II) $R^1$ is a linear or branched, saturated or unsaturated $C_1$-$C_{32}$ alkyl (preferably $C_2$-$C_{20}$ alkyl and in particular Ca-GIs alkyl), AO is ethyleneoxy, propyleneoxy, butyleneoxy, or mixtures thereof, n is any value from 1 to 20, and m is any value from 3 to 80. In another preferred form of the alkoxylate of the formula (II) $R^1$ is a linear or branched, saturated or unsaturated $C_6$-$C_{32}$ alkyl (preferably $C_8$-$C_{20}$ alkyl and in particular $C_{10}$-$C_{18}$ alkyl), AO is ethyleneoxy, propyleneoxy, butyleneoxy, or mixtures thereof, n is any value from 1 to 20, and m is any value from 3 to 80.

AO is usually a saturated or unsaturated, linear or branched $C_2$-$C_6$ alkyleneoxy group. Mixtures of different $C_2$-$C_6$ alkyleneoxy group are also possible (e.g. AO is a mixture of ethyleneoxy and a $C_3$-$C_6$ alkyleneoxy group, wherein a mixture of ethyleneoxy and propyleneoxy is preferred). Examples for AO are ethyleneoxy, propyleneoxy, butyleneoxy, or mixtures thereof. AO is more preferably ethyleneoxy, propyleneoxy, or a mixture thereof. In particular, AO is ethyleneoxy (e.g. as in formula (III) below).

The index n is usually any value from 1 to 30, preferably from 1 to 20, more preferably from 1 to 10, and in particular from 1 to 7. In another form n is from 1.1 to 30, preferably from 1.5 to 20.

The index m is usually any value from 1 to 200, preferably from 2 to 100, more preferably from 3 to 80, and in particular from 5 to 60. In another form the index m is usually any value from 2 to 200.

In a preferred form, $R^1$ is a linear or branched, saturated or unsaturated $C_1$-$C_{32}$ alkyl (preferably $C_2$-$C_{20}$ alkyl and in particular $C_{10}$-$C_{18}$ alkyl), $R^2$ is a linear, saturated $C_2$-$C_{20}$ alkylene, AO is ethyleneoxy, propyleneoxy, butyleneoxy, or mixtures thereof, n is any value from 1 to 20, and m is any value from 3 to 80. In more preferred form, $R^1$ is a linear or branched, saturated or unsaturated $C_6$-$C_{32}$ alkyl (preferably $C_8$-$C_{20}$ alkyl and in particular $C_{10}$-$C_{18}$ alkyl), $R^2$ is a linear, saturated $C_3$-$C_{15}$ alkylene, AO is ethyleneoxy, propyleneoxy, butyleneoxy, or mixtures thereof, n is any value from 1 to 20, and m is any value from 3 to 80. In particular preferred form, $R^1$ is a linear or branched, saturated $C_6$-$C_{32}$ alkyl (preferably $C_8$-$C_{20}$ alkyl and in particular $C_{10}$-$C_{18}$ alkyl), $R^2$ is a linear, saturated $C_4$-$C_8$ alkylene, AO is ethyleneoxy, propyleneoxy or mixtures thereof, n is any value from 1 to 20, and m is any value from 3 to 80.

In a particular preferred embodiment, the alkoxylate is an alkoxylate of the formula (III)

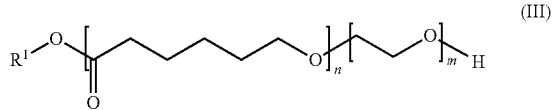

(III)

where $R^1$ is a $C_1$-$C_{32}$ hydrocarbon group, n is from 1 to 30, and m is from 1 to 200. Preferably, $R^1$ is a linear or branched, saturated or unsaturated $C_1$-$C_{32}$ alkyl (preferably $C_2$-$C_{20}$ alkyl and in particular $C_{10}$-$C_{18}$ alkyl), n is any value from 1 to 20, and m is any value from 3 to 80. In another particular preferred embodiment, the alkoxylate is an alkoxylate of the formula (III), where $R^1$ is a $C_6$-$C_{32}$ hydrocarbon group, n is from 1 to 30, and m is from 2 to 200. Preferably, $R^1$ is a linear or branched, saturated or unsaturated $C_6$-$C_{32}$ alkyl (preferably $C_8$-$C_{20}$ alkyl and in particular $C_{10}$-$C_{18}$ alkyl), n is any value from 1 to 20, and m is any value from 3 to 80.

The alkoxylate of the formula (I) may be prepared by known methods. In a first step, an alcohol $R^1$—OH may react with an lacton (such as ε-caprolactone to form the alkoxylate of the formula (II)) according to U.S. Pat. No. 3,284,417. In a second step, the product of the first step is alkoxylate, e.g. with alkylene oxide. The alkoxylation may be catalyzed by strong bases such as alkali metal hydroxides and alkaline earth metal hydroxides, Brönsted acids or Lewis acids, such as $AlCl_3$, $BF_3$ and the like. Catalysts such as hydrotalcite or DMC may be used for alcohol oxylates with a narrow distribution. The alkoxylation is preferably carried out at temperatures in the range of from approximately 80 to 250° C., preferably approximately 100 to 220° C. The pressure range is preferably between atmospheric pressure and 600 bar. If desired, the alkylene oxide may comprise an admixture of inert gas, for example of from approximately 5 to 60%.

The composition may contain at least 0.1 wt %, preferably at least 1 wt % of the alkoxylate. The composition according to the invention may be present as an agrochemical composition type and comprises from 1 to 80% by weight of the alkoxylate, preferably from 2 to 50% by weight and in particular from 5 to 30% by weight.

The term pesticide refers to at least one active substance selected from the group of the fungicides, insecticides, nematicides, herbicides, safeners and/or growth regulators. Preferred pesticides are fungicides, insecticides, herbicides and growth regulators. Especially preferred pesticides are growth regulators. Mixtures of pesticides of two or more of the abovementioned classes may also be used. The skilled worker is familiar with such pesticides, which can be found, for example, in the Pesticide Manual, 15th Ed. (2009), The British Crop Protection Council, London. Suitable insecticides are insecticides from the class of the carbamates, organophosphates, organochlorine insecticides, phenylpyrazoles, pyrethroids, neonicotinoids, spinosins, avermectins, milbemycins, juvenile hormone analogs, alkyl halides, organotin compounds nereistoxin analogs, benzoylureas, diacylhydrazines, METI acarizides, and insecticides such as chloropicrin, pymetrozin, flonicamid, clofentezin, hexythiazox, etoxazole, diafenthiuron, propargite, tetradifon, chlorofenapyr, DNOC, buprofezine, cyromazine, amitraz, hydramethylnon, acequinocyl, fluacrypyrim, rotenone, or their derivatives. Suitable fungicides are fungicides from the classes of dinitroanilines, allylamines, anilinopyrimidines, antibiotics, aromatic hydrocarbons, benzenesulfonamides, benzimidazoles, benzisothiazoles, benzophenones, benzothiadiazoles, benzotriazines, benzyl carbamates, carbamates, carboxamides, carboxylic acid diamides, chloronitriles cyanoacetamide oximes, cyanoimidazoles, cyclopropanecarboxamides, dicarboximides, dihydrodioxazines, dinitrophenyl crotonates, dithiocarbamates, dithiolanes, ethylphosphonates, ethylaminothiazolecarboxamides, guanidines, hydroxy-(2-amino)pyrimidines, hydroxyanilides, imidazoles, imidazolinones, inorganic substances, isobenzofuranones, methoxyacrylates, methoxycarbamates, morpholines, N phenylcarbamates, oxazolidinediones, oximinoacetates, oximinoacetamides, peptidylpyrimidine nucleosides, phenylacetamides, phenylamides, phenylpyrroles, phenylureas, phosphonates, phosphorothiolates, phthalamic acids, phthalimides, piperazines, piperidines, propionamides, pyridazinones, pyridines, pyridinylmethylbenzamides, pyrimidinamines, pyrimidines, pyrimidinonehydrazones, pyrroloquinolinones, quinazolinones, quinolines, quinones, sulfamides, sulfamoyltriazoles, thiazolecarboxamides, thiocarbamates, thiophanates, thiophenecarboxamides, toluamides, triphenyltin compounds, triazines, triazoles. Suitable herbicides are herbicides from the classes of the acetamides, amides, aryloxyphenoxypropionates, benzamides, benzofuran, benzoic acids, benzothiadiazinones, bipyridylium, carbamates, chloroacetamides, chlorocarboxylic acids, cyclohexanediones, dinitroanilines, dinitrophenol, diphenyl ether, glycines, imidazolinones, isoxazoles, isoxazolidinones, nitriles, N-phenylphthalimides, oxadiazoles, oxazolidinediones, oxyacetamides, phenoxycarboxylic acids, phenylcarbamates, phenylpyrazoles, phenylpyrazolines, phenylpyridazines, phosphinic acids, phosphoroamidates, phosphorodithioates, phthalamates, pyrazoles, pyridazinones, pyridines, pyridinecarboxylic acids, pyridinecarboxamides, pyrimidinediones, pyrimidinyl(thio)benzoates, quinolinecarboxylic acids, semicarbazones, sulfonylaminocarbonyltriazolinones, sulfonylureas, tetrazolinones, thiadiazoles, thiocarbamates, triazines, triazinones, triazoles, triazolinones, triazolocarboxamides, triazolopyrimidines, triketones, uracils, ureas.

Preferably, the pesticide is soluble in water up to 10 g/l, preferably up to 1 g/l, and in particular up to 0.5 g/l, at 20° C.

The composition according to the invention may also be present in form of an agrochemical compositions comprising the pesticide, the alkoxylate of the formula (I), and optionally an auxiliary. An agrochemical composition comprises a pesticidally effective amount of a pesticide. The term "effective amount" denotes an amount of the composition or of the compounds I, which is sufficient for controlling harmful pests on or around cultivated plants or in the protection of materials and which does not result in a substantial damage to the treated plants. Such an amount can vary in a broad range and is dependent on various factors, such as the fungal species to be controlled, the treated cultivated plant or material, the climatic conditions and the specific pesticide used.

Suitable, customary types of agrochemical compositions are e. g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Monograph No. 2, 6$^{th}$ Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Examples for suitable auxiliaries are solvents, liquid carriers, solid carriers or fillers, surfactants, dispersants, emulsifiers, wetters, further adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharide powders, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emusifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylate surfactants, N-substituted fatty acid amides, amine oxides, esters, sugar-based surfactants, polymeric surfactants, and mixtures thereof. Examples of alkoxylate surfactants are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable further adjuvants are compounds, which have a neglectable or even no pesticidal activity themselves, and which improve the biological performance of the pesticide on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for composition types and their preparation are:
i) Water-Soluble Concentrates (SL, LS)
10-60 wt % of the pesticide and 5-15 wt % wetting agent (e.g. alcohol alkoxylates) are dissolved in water and/or in a water-soluble solvent (e.g. alcohols) up to 100 wt %. The active substance dissolves upon dilution with water.
ii) Dispersible Concentrates (DC)
5-25 wt % of the pesticide and 1-10 wt % dispersant (e. g. polyvinylpyrrolidone) are dissolved in up to 100 wt % organic solvent (e.g. cyclohexanone). Dilution with water gives a dispersion.

iii) Emulsifiable Concentrates (EC)

15-70 wt % of the pesticide and 5-10 wt % emulsifiers (e.g. calcium dodecylbenzenesulfonate and castor oil ethoxylate) are dissolved in up to 100 wt % water-insoluble organic solvent (e.g. aromatic hydrocarbon). Dilution with water gives an emulsion.

iv) Emulsions (EW, EO, ES)

5-40 wt % of the pesticide and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into up to 100 wt % water by means of an emulsifying machine and made into a homogeneous emulsion. Dilution with water gives an emulsion.

v) Suspensions (SC, OD, FS)

In an agitated ball mill, 20-60 wt % of the pesticide are comminuted with addition of 2-10 wt % dispersants and wetting agents (e.g. sodium lignosulfonate and alcohol ethoxylate), 0.1-2 wt % thickener (e.g. xanthan gum) and up to 100 wt % water to give a fine active substance suspension. Dilution with water gives a stable suspension of the active substance. For FS type composition up to 40 wt % binder (e.g. polyvinylalcohol) is added.

vi) Water-Dispersible Granules and Water-Soluble Granules (WG, SG)

50-80 wt % of the pesticide are ground finely with addition of up to 100 wt % dispersants and wetting agents (e.g. sodium lignosulfonate and alcohol ethoxylate) and prepared as water-dispersible or water-soluble granules by means of technical appliances (e. g. extrusion, spray tower, fluidized bed). Dilution with water gives a stable dispersion or solution of the active substance.

vii) Water-Dispersible Powders and Water-Soluble Powders (WP, SP, WS)

50-80 wt % of the pesticide are ground in a rotor-stator mill with addition of 1-5 wt % dispersants (e.g. sodium lignosulfonate), 1-3 wt % wetting agents (e.g. alcohol ethoxylate) and up to 100 wt % solid carrier, e.g. silica gel. Dilution with water gives a stable dispersion or solution of the active substance.

viii) Gel (GW, GF)

In an agitated ball mill, 5-25 wt % of the pesticide are comminuted with addition of 3-10 wt % dispersants (e.g. sodium lignosulfonate), 1-5 wt % thickener (e.g. carboxymethylcellulose) and up to 100 wt % water to give a fine suspension of the active substance. Dilution with water gives a stable suspension of the active substance.

iv) Microemulsion (ME)

5-20 wt % of the pesticide are added to 5-30 wt % organic solvent blend (e.g. fatty acid dimethylamide and cyclohexanone), 10-25 wt % surfactant blend (e.g. alcohol ethoxylate and arylphenol ethoxylate), and water up to 100%. This mixture is stirred for 1 h to produce spontaneously a thermodynamically stable microemulsion.

iv) Microcapsules (CS)

An oil phase comprising 5-50 wt % of the pesticide, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of the pesticide, 0-40 wt % water insoluble organic solvent (e.g. aromatic hydrocarbon), and an isocyanate monomer (e.g. diphenylmethene-4,4'-diisocyanatae) are dispersed into an aqueous solution of a protective colloid (e.g. polyvinyl alcohol). The addition of a polyamine (e.g. hexamethylenediamine) results in the formation of a polyurea microcapsules. The monomers amount to 1-10 wt %. The wt % relate to the total CS composition.

ix) Dustable Powders (DP, DS)

1-10 wt % of the pesticide are ground finely and mixed intimately with up to 100 wt % solid carrier, e.g. finely divided kaolin.

x) Granules (GR, FG)

0.5-30 wt % of the pesticide is ground finely and associated with up to 100 wt % solid carrier (e.g. silicate). Granulation is achieved by extrusion, spray-drying or the fluidized bed.

xi) Ultra-Low Volume Liquids (UL)

1-50 wt % of the pesticide are dissolved in up to 100 wt % organic solvent, e.g. aromatic hydrocarbon.

The compositions types i) to xi) may optionally comprise further auxiliaries, such as 0.1-1 wt % bactericides, 5-15 wt % anti-freezing agents, 0.1-1 wt % anti-foaming agents, and 0.1-1 wt % colorants. Preferred composition type is a suspension concentrate.

The agrochemical compositions generally comprise between 0.01 and 95%, preferably between 0.1 and 90%, and most preferably between 0.5 and 75%, by weight of active substance (i.e. pesticide). The active substances are employed in a purity of from 90% to 100%, preferably from 95% to 100% (according to NMR spectrum).

Water-soluble concentrates (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The compositions in question give, after two-to-tenfold dilution, active substance concentrations of from 0.01 to 60% by weight, preferably from 0.1 to 40% by weight, in the ready-to-use preparations. Application can be carried out before or during sowing. Methods for applying or treating the pesticide and compositions thereof, respectively, on to plant propagation material, especially seeds include dressing, coating, pelleting, dusting, soaking and in-furrow application methods of the propagation material. Preferably, the pesticide or the compositions thereof, respectively, are applied on to the plant propagation material by a method such that germination is not induced, e. g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, in particular from 0.1 to 0.75 kg per ha.

In treatment of plant propagation materials such as seeds, e. g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seed) are generally required.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and other pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

The concentration of the alkoxylate of the formula (I) in the ready-to-use preparation (e.g. the tank mix) is in most cases in the range of from 0.01 to 50 g/l, preferably 0.08 to 10 g/l and in particular 0.5 to 8 g/l.

The concentration of water in the ready-to-use preparation (e.g. the tank mix) is in most cases at least 60 wt %, preferably at least 75 wt %, and in particular at least 90 wt %.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank and further auxiliaries may be added, if appropriate.

In a further embodiment, either individual components of the composition according to the invention or partially premixed components, e. g. components comprising the pesticide and the adjuvant, may be mixed by the user in a spray tank and further auxiliaries and additives may be added, if appropriate. In a further embodiment, either individual components of the composition according to the invention or partially premixed components, e. g. components comprising the pesticide and/or the adjuvant can be applied jointly (e.g. after tank mix) or consecutively.

The present invention furthermore relates to a method of preparing the composition according to the invention by bringing the adjuvant and the pesticide into contact, e.g. by mixing. The contacting may be done between 5 to 95° C. Thus, a tankmix or a agrochemical composition may be prepared.

The present invention furthermore relates to a method of controlling phytopathogenic fungi and/or undesired plant growth and/or undesired insect or mite attack and/or for regulating the growth of plants, wherein the composition according to the invention or the adjuvant is allowed to act on the respective pests, their environment or the crop plants to be protected from the respective pest, on the soil and/or on undesired plants and/or on the crop plants and/or on their environment.

Examples of suitable crop plants are cereals, for example wheat, rye, barley, triticale, oats or rice; beet, for example sugar or fodder beet; pome fruit, stone fruit and soft fruit, for example apples, pears, plums, peaches, almonds, cherries, strawberries, raspberries, currants or gooseberries; legumes, for example beans, lentils, peas, lucerne or soybeans; oil crops, for example oilseed rape, mustard, olives, sunflowers, coconut, cacao, castor beans, oil palm, peanuts or soybeans; cucurbits, for example pumpkins/squash, cucumbers or melons; fiber crops, for example cotton, flax, hemp or jute; citrus fruit, for example oranges, lemons, grapefruit or tangerines; vegetable plants, for example spinach, lettuce, asparagus, cabbages, carrots, onions, tomatoes, potatoes, pumpkin/squash or capsicums; plants of the laurel family, for example avocados, cinnamon or camphor; energy crops and industrial feedstock crops, for example maize, soybeans, wheat, oilseed rape, sugar cane or oil palm; maize; tobacco; nuts; coffee; tea; bananas; wine (dessert grapes and grapes for vinification); hops; grass, for example turf; sweetleaf (*Stevia rebaudania*); rubber plants and forest plants, for example flowers, shrubs, deciduous trees and coniferous trees, and propagation material, for example seeds, and harvested produce of these plants.

The term crop plants also includes those plants which have been modified by breeding, mutagenesis or recombinant methods, including the biotechnological agricultural products which are on the market or in the process of being developed. Genetically modified plants are plants whose genetic material has been modified in a manner which does not occur under natural conditions by hybridizing, mutations or natural recombination (i.e. recombination of the genetic material). Here, one or more genes will, as a rule, be integrated into the genetic material of the plant in order to improve the plant's properties. Such recombinant modifications also comprise posttranslational modifications of proteins, oligo- or polypeptides, for example by means of glycosylation or binding polymers such as, for example, prenylated, acetylated or farnesylated residues or PEG residues.

The present invention also relates to seed (such as seeds or other plant propagation materials) comprising the composition according to the invention. Plant propagation materials can be treated preventively with the composition according to the invention at the point of or even before sowing or at the point of or even before transplanting. For the treatment of seed, one will generally use water-soluble concentrates (LS), suspensions (FS), dusts (DS), water-dispersible and water-soluble powders (WS, SS), emulsions (ES), emulsifiable concentrates (EC) and gels (GF). These compositions can be applied to the propagation materials, in particular seed, in undiluted form or, preferably, in diluted form. Here, the composition in question can be diluted 2- to 10-fold, so that from 0.01 to 60% by weight, preferably from 0.1 to 40% by weight, of active substance is present in the compositions used for the seed dressing. The application may be effected before or during sowing. The treatment of plant propagation material, in particular the treatment of seed, is known to the skilled worker and carried out by dusting, coating, pelleting, dipping or soaking the plant propagation material, the treatment preferably being carried out by pelleting, coating and dusting or by in-furrow treatment so that, for example, untimely early germination of the seed is prevented. It is preferred to use suspensions for the treatment of seed. Usually, such compositions comprise from 1 to 800 g/l of active substance, from 1 to 200 g/l of surfactants, from 0 to 200 g/l of antifreeze agents, from 0 to 400 g/l of binders, from 0 to 200 g/l of colorants and solvent, preferably water.

The advantages of the invention are high stability of the formulation and of the spray mixture, little wind-caused drift in the case of spray applications, good adhesion of the formulation on the surface of the treated plants, increased solubility of the pesticides in the formulation, increased uptake of the pesticides into the plant, or more rapid and enhanced activity. Another advantage is the high biodegradability of the alkoxylate. An important advantage is the low toxicity of the alkoxylate, the ability of the alkoxylate to lower the surface tension of aqueous compositions, or the increased spreading on plant surfaces. Another advantage is the presence of a hydrolysable group (the carboxylic ester group) in the alkoxylate. Another advantage is the low harmful effect against crop plants, i.e. low phytotoxic effects.

The examples which follow illustrate the invention without imposing any limitation.

EXAMPLE 1-7

Alcohol+Lactone

An alcohol was reacted with ϵ-caprolactone at 140 to 180° C. under nitrogen according to U.S. Pat. No. 3,284,417. The resulting esters were received with yield of at least 95%. The alcohols and the molar ratios are summarized in Table 1. Isotridecanol N is a mixture of isomeric isotridecanol (CAS 27458-92-0) and commercially available from BASF SE.

TABLE 1

| Example | Alcohol | Amount of Alcohol | Molar Ratio Alcohol/Lactone |
|---|---|---|---|
| 1 | 1-Hexadecanol | 299 g | 1/5 |
| 2 | 1-Hexadecanol | 258 g | 1/2 |
| 3 | Isotridecanol N | 467 g | 1/2 |
| 4 | 2-Propylheptanol | 267 g | 1/0.7 |
| 5 | 2-Propylheptanol | 500 g | 1/1.4 |
| 6 | 2-Propylheptanol | 579 g | 1/1 |
| 7 | 2-Propylheptanol | 405 g | 1/2 |

EXAMPLE 8-14

Ethoxylation

The esters which were prepared in Examples 1-7 were ethoxylated by reacting them with ethylene oxide (EO) in the presence of 250 ppm DMC catalyst at about 130° C. The molar ratio of ester and ethylene oxide, and the hydroxy number of the resulting alkoxylate are summarized in Table 2. The alkoxylate were obtained in quantitative yield. The molecular weight was calculated based on the OH value.

TABLE 2

Preparation of alkoxylates

| Example | Ester from Example | Amount of Ester | Molar ratio Ester/EO | OH value [mg KOH/g] | Molecular weight |
|---|---|---|---|---|---|
| 8 | 1 | 121.4 g | 1/18 | 37 | 1500 |
| 9 | 2 | 91.4 g | 1/18 | 47 | 1186 |
| 10 | 3 | 46.2 g | 1/50 | 28 | 2011 |
| 11 | 4 | 113.5 g | 1/8 | 83 | 676 |
| 12 | 5 | 96.5 g | 1/8 | 93 | 603 |
| 13 | 6 | 142.4 g | 1/8 | 114 | 491 |
| 14 | 7 | 142.2 g | 1/8 | 87 | 647 |

EXAMPLE 15

Uptake Enhancement for Epoxiconazol

The uptake study was done with a spray solution prepared from an aqueous suspension concentrate containing 125 g/l epoxiconazole. The alkoxylates from Examples 8 to 14 were added in form of a 50 wt % composition in aromatic hydrocarbons (Bp>230° C.), dodecylbenzol-sulfonat, and ethoxylated castor oil. The application rate was 125 g active per ha in 300 liter water. The alkoxylate samples were added with 250 g/ha.

Uptake measurements have been carried out with the secondary leaf of wheat plants (*Triticum aestivum* cultivar Cubus) from the greenhouse (growth state 12 BBCH). Three droplets with 1 μL spray solution were pipetted on the leaf surface. Three different leaves were treated. After drying of the spray residues the plants were further cultivated for 7 d at 80% relative humidity in a light-climate chamber. After 7 days the leaves were analyzed by treating with cellulose acetate to find residues on the surface of the leaves.

50 μl cellulose acetate (5% in acetone) was applied as a thin film on the treated leaf. After drying of the cellulose acetate the film was completely removed with tweezers. The residue was solubilized in 500 μl acetone. Subsequently 500 μl petrol ether was added to precipitate the cellulose acetate. The vial was centrifuged and the supernatant was transferred in an HPLC vial and dried. The residue was solubilized in 1 ml methanol and were analyzed for the active by LC-MS-MS. Aliquots of the formulation were directly measured in the LC-MS-MS to have a recovery factor. The results are summarized in Table 3.

TABLE 3

Uptake rate

| Alkoxylate from Example | Uptake rate [%] |
|---|---|
| —[a] | 6 |
| 8 | 37 |
| 9 | 39 |
| 10 | 27 |
| 11 | 24 |
| 12 | 25 |
| 13 | 32 |
| 14 | 34 |

[a]Comparative experiment

EXAMPLE 16

Uptake Enhancement for Xemium®

The uptake study was done with a spray solution prepared from an aqueous suspension concentrate of Xemium® (commercially available as Sercadis® from BASF Corp., containing 300 g/l fluxapyroxad) as described in Example 15. The results are summarized in Table 4.

TABLE 4

Uptake rate

| Alkoxylate from Example | Uptake rate [%] |
|---|---|
| —[a] | 3 |
| 8 | 19 |
| 9 | 22 |
| 10 | 13 |
| 11 | 7 |
| 12 | 14 |
| 13 | 15 |
| 14 | 18 |

[a]Comparative experiment

The invention claimed is:

1. A composition comprising a pesticide and an alkoxylate of the formula (I)

$$R^1\text{-}O\text{-}\underset{O}{\overset{\|}{C}}\text{-}R^2\text{-}[O]_n\text{-}[AO]_m\text{-}H \quad (I)$$

where $R^1$ is a $C_6$-$C_{32}$ hydrocarbon group, $R^2$ is a $C_5$ alkylene group, AO is $C_2$-$C_6$ alkyleneoxy group, n is from 1 to 30, and m is from 2 to 200.

2. The composition according to claim 1, wherein $R^1$ is an linear or branched, saturated or unsaturated $C_8$-$C_{20}$ alkyl.

3. The composition according to claim 1, wherein m is from 3 to 80.

4. The composition according to claim 1, wherein AO is ethylenoxy, propyleneoxy, or a mixture of both.

5. The composition according to claim 1, wherein AO is ethylenoxy.

6. The composition according to claim 1 containing 0.5 to 50 wt % of the alkoxylate.

7. A method of preparing the composition according to claim 1, comprising bringing the pesticide and the alkoxylate of the formula (I) into contact with the alkoxylate.

8. An alkoxylate of the formula (I)

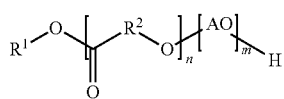
(I)

where $R^1$ is a $C_6$-$C_{32}$ hydrocarbon group, $R^2$ is a $C_5$ alkylene group, AO is $C_2$-$C_6$ alkyleneoxy group, n is from 1 to 30, and m is from 2 to 200.

9. The alkoxylate according to claim 8, wherein $R^1$ is a linear or branched, saturated or unsaturated $C_8$-$C_{20}$ alkyl.

10. The alkoxylate according to claim 8, wherein AO is ethylenoxy, propyleneoxy, or a mixture of both.

11. A method of controlling phytopathogenic fungi and/or undesired plant growth and/or undesired insect or mite attack and/or for regulating the growth of plants, wherein the composition according to claim 1 is allowed to act on the respective pests, their environment or the crop plants to be protected from the respective pest, on the soil and/or on undesired plants and/or on the crop plants and/or on their environment.

12. Seed treated with the composition according to claim 1.

13. The method of claim 11, wherein $R^1$ of the alkoxylate is an linear or branched, saturated or unsaturated $C_8$-$C_{20}$ alkyl.

14. The method of claim 11, wherein m of the alkoxylate is from 3 to 80.

15. The method of claim 11, wherein AO of the alkoxylate is ethylenoxy, propyleneoxy, or a mixture of both.

16. The method of claim 11, wherein AO of the alkoxylate is ethylenoxy.

17. The method of claim 11 containing 0,5 to 50 wt % of the alkoxylate.

* * * * *